(12) United States Patent
Cheim

(10) Patent No.: US 8,964,186 B2
(45) Date of Patent: Feb. 24, 2015

(54) OPTICS SENSOR STRUCTURE FOR DETECTING WATER OR OIL LEAKAGE INSIDE A CONSERVATOR HAVING A BLADDER OR MEMBRANE

(71) Applicant: Luiz A. V. Cheim, St. Charles, MO (US)

(72) Inventor: Luiz A. V. Cheim, St. Charles, MO (US)

(73) Assignee: ABB Technology AG, Zürich (CH)

(*) Notice: Subject to any disclaimer, the term of this patent is extended or adjusted under 35 U.S.C. 154(b) by 0 days.

(21) Appl. No.: 14/073,903

(22) Filed: Nov. 7, 2013

(65) Prior Publication Data

US 2014/0077072 A1 Mar. 20, 2014

Related U.S. Application Data

(62) Division of application No. 13/539,527, filed on Jul. 2, 2012, now Pat. No. 8,654,338.

(60) Provisional application No. 61/506,213, filed on Jul. 11, 2011.

(51) Int. Cl.
*G01N 21/55* (2014.01)
*G01N 21/01* (2006.01)
*G01M 3/38* (2006.01)

(52) U.S. Cl.
CPC ........ *G01N 21/01* (2013.01); *G01M 3/38* (2013.01)
USPC ........................................... 356/445; 356/448

(58) Field of Classification Search
USPC .......... 356/445, 446, 448, 234, 410, 415, 249
See application file for complete search history.

(56) References Cited

FOREIGN PATENT DOCUMENTS

| GB | 1051462 A | 12/1966 |
|---|---|---|
| JP | 60040934 A | 3/1985 |
| JP | 2008249617 A | 10/2008 |
| WO | 2011079357 A1 | 7/2011 |

OTHER PUBLICATIONS

PCT Search Report & Written Opinion in PCT/US2012/045183 dated Feb. 20, 2013.

*Primary Examiner* — Tri T Ton
(74) *Attorney, Agent, or Firm* — Manelli Selter PLLC; Edward J. Stemberger

(57) ABSTRACT

Optical sensor structure senses the presence of liquid in a sealed conservator tank. The sensor structure includes a sensor head having a body with first and second opposing ends, a plurality of perforations through the body and spaced between the first and second ends, and a mirror disposed at the second end. The perforations are constructed and arranged to receive and hold fluid therein. The sensor head is constructed and arranged to rest on a surface of a bladder. The sensor structure includes a light source, a first fiber optic cable between the light source and the first end of the body, a light detector, and a second fiber optic cable between the light detector and the first end of the body. The amount of light received by the light detector is reduced when liquid, instead of air, is in at least some of the perforations in the body.

5 Claims, 1 Drawing Sheet

OPTICS SENSOR STRUCTURE FOR DETECTING WATER OR OIL LEAKAGE INSIDE A CONSERVATOR HAVING A BLADDER OR MEMBRANE

FIELD

The invention relates to transformers and, more particularly, to transformer having a conservator oil preservation system (COPS) having a bladder or a membrane, with a sensor being provided on the bladder to detect moisture on top of the bladder and/or failure of the bladder.

BACKGROUND

In the oil preservation type system, a synthetic rubber bladder, is stretched over the surface of the oil in a conservator tank to completely isolate the insulating oil from outside air. The bladder shape varies according to expansion and contraction of the oil, maintaining pressure in the bladder at atmospheric pressure. Since the bladder completely isolates the oil from the atmosphere, absent a failure of the bladder, there is no possibility for oxygen or moisture penetrating the oil. Accumulation of water in a conservator tank can contaminate the oil or can even cause confusion with respect to the oil level indication if one believes the bladder is operating properly.

Since the conservator tanks are sealed, it is difficult to access the inside of the tank to ensure that the bladder is functioning properly to isolate the oil from the air. Thus, there is a need to provide a sensor associated with the bladder to detect the presence of any moisture or oil on top of the bladder inside of the conservator tank.

SUMMARY

An object of the invention is to fulfill the need referred to above. In accordance with the principles of the present invention, this objective is achieved by providing optical sensor structure for sensing the presence of liquid in a sealed conservator tank. The tank includes a bladder isolating oil from air. The bladder has a first surface exposed to the air and an opposing second surface exposed to the oil. The sensor structure includes a sensor head having a body with first and second opposing ends, a plurality of perforations through the body and spaced between the first and second ends, and a mirror disposed at the second end. The perforations are constructed and arranged to receive and hold fluid therein. The sensor head is constructed and arranged to rest on the first surface of the bladder. The sensor structure includes a light source, a first fiber optic cable between the light source and the first end of the body, a light detector, and a second fiber optic cable between the light detector and the first end of the body. Wherein, when the light source provides light through the first fiber optic cable and to the perforated body, the light reflects off the mirror and is received by the second fiber optic cable and by the light detector. The amount of light received by the light detector is reduced when liquid, instead of air, is in at least some of the perforations in the body.

In accordance with yet another aspect of the invention, a method detects the presence of liquid on an air side of a bladder disposed in a conservator tank for a transformer oil preservation type system. The bladder isolates oil from air and has a first surface exposed to the air and an opposing, second surface exposed to the oil. The method places an optical sensor head on the first surface of the bladder. A source of light is provided to the sensor head. A normal condition is determined when no liquid is in contact with the sensor head by detecting a certain amount of light exiting the sensor head. A malfunction condition is determined when liquid is in contact with the sensor head by detecting an amount of light, less than the certain amount of light, exiting the sensor head.

Other objects, features and characteristics of the present invention, as well as the methods of operation and the functions of the related elements of the structure, the combination of parts and economics of manufacture will become more apparent upon consideration of the following detailed description and appended claims with reference to the accompanying drawings, all of which form a part of this specification.

BRIEF DESCRIPTION OF THE DRAWINGS

The invention will be better understood from the following detailed description of the preferred embodiments thereof, taken in conjunction with the accompanying drawings wherein like numbers indicate like parts, in which.

DETAILED DESCRIPTION OF THE EXEMPLARY EMBODIMENTS

Figure 1:
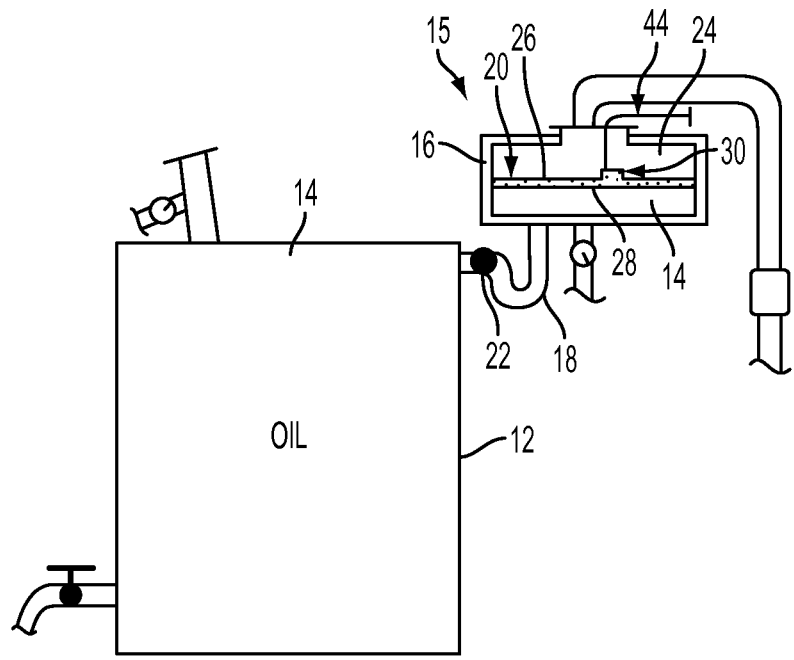
FIG. 1 is a schematic view of a conservator tank fluidly coupled with a transformer tank, with optical sensor structure provided on a bladder in the conservator tank, in accordance with the present invention.

With reference to FIG. 1, transformer oil preservation type system includes a transformer tank 12 that is filled with insulating oil 14 to insulate components therein, such as a tap changer (not shown). A conservator tank structure, generally indicated at 15, includes a conservator tank 16 fluidly connected via piping 18 with the transformer tank 12. A Buchholz relay 22 is provided in piping 18 in the conventional manner. An air-filled bladder 20 is stretched over the surface of the oil 14 in the conservator tank 16 to completely isolate the insulating oil from outside, dry air 24 air. Thus, the bladder 20 has a first surface 26 exposed to the dry air 24 and an opposing second surface 28 contacting or resting on the oil 14. As used herein, "bladder" can be an air cell, membrane, rubber bag, or any other structure that can contain air and vary in shape. In the conventional manner, the bladder 20 shape varies according to expansion and contraction of the oil 14, maintaining pressure in the bladder 20 at atmospheric pressure.

In accordance with the embodiment, in order to detect the presence of water and/or oil that has leaked past the bladder 20 due to a malfunction, tear-off, rupture, infiltration, etc., optical sensor structure, generally indicated at 30, is provided on the first or upper surface 26 of the bladder.

Figure 2:
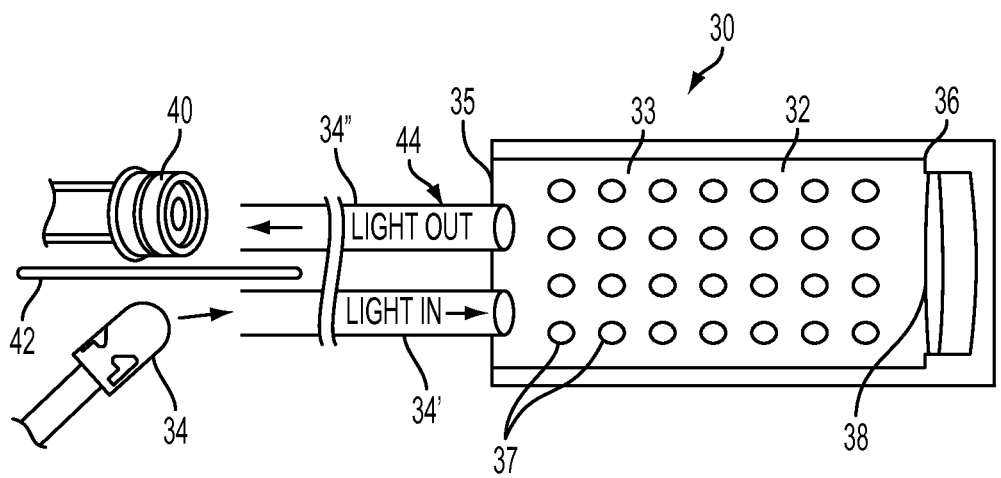
FIG. 2 is an enlarged view of the sensor structure of FIG. 1.

As best shown in FIG. 2, the sensor structure 30 detects light reflected from a sensor head 32, when there is no moisture or insulating oil which would block the free path of light rays. The sensor structure 30 includes a simple light emitting diode (LED) 34 as a light source that is preferably located outside of the tank 16 at the transformer control cabinet (not shown). The LED 34 emits light which travels through fiber optics, generally indicated at 44, inside of the sealed conservator tank 16 and connected to a first end 35 of the sensor head 32. The fiber optics 44 is preferably an input fiber optic cable 34' made of glass or plastic. The light-weight, sensor head 32 includes a preferably plastic body 33 having first and second opposing ends, 35, 36. A plurality of perforations 37 are provided through the body 33 and are spaced between the ends 35, 36. The perforations 37 can receive and hold (by submersion or surface tension) oil or water that may have leaked to be above the upper surface 26 of the bladder 20 due to bladder malfunction or infiltration, as discussed above.

Thus, the leaking oil or water that enters at least some of the perforations 37 blocks or greatly reduces the light ray reflection at a flat mirror 38 disposed at the second end 36 of the sensor head 32. This light reduction results because water and oil have a greater refractive index than air (which is in the perforations 37 when water and/or oil are not present). The reduced reflected light is captured by the fiber optics 34 (such as output fiber optic cable 34") which is connected to a light detector 40, preferably in the form of a photodiode or any other photo detector. The light detector 40 provides an electrical analogue output (voltage signal) any time that there is light on the surface of the detector 40. If no or reduced light is received by the light detector 40, a low voltage level is output by the light detector 40, which indicates that the perforations 37 in the sensor head 32 contain liquid (water/oil) and thus there may be a malfunction of the bladder 20. In the absence of any liquid inside the perforations 37 of the sensor head 32, the light rays emitted by the LED 34 reflect back from the surface of the mirror 38 and are captured by the fiber optic cable 34" and thus the light detector 40. Normal voltage output indicates that air only is inside the perforations in the sensor head (a normal operating condition with no bladder 20 malfunction).

Optical insulation 42 is provided to optically isolate the LED 34 from the light detector 40 to avoid interference and sensor error. For example, the LED 34 and light detector 40 are preferably located in a self-contained sensor box (defining the optical insulation), in the transformer control cabinet, where the minimum electronics required to power up the sensor structure 30 will be available (any DC power supply converted to a 5V DC or 12V DC power supply). Thus, the fiber optic cables 34', 34" are elongated to space the light source 34 and the light detector 40 remotely from the sensor head 32.

Thus, the very light-weight sensor structure 30 using fiber optics 34 provides a cost-effective and efficient way to detect if water and/or oil is present on the upper surface 26 of a bladder 20 of a conservator tank 16. The sensor structure 20 does not interfere electrically (no current needed in tank 16), chemically or mechanically (weight of sensor head 32 does not affect function of bladder 20), with any of the power transformer operating parameters. The sensor structure 30 can be installed on the upper surface 26 of the bladder 20 in a new conservator tank, or can be dropped onto the upper surface 26 of the bladder 20 in an existing conservator tank 16 during outages.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. A method of detecting the presence of liquid on an air side of a bladder disposed in a conservator tank for a transformer oil preservation type system, the bladder isolating oil from air and having a first surface exposed to the air and an opposing, second surface exposed to the oil, the method comprising the steps of:
    placing an optical sensor head on the first surface of the bladder,
    providing a source of light to the sensor head,
    determining a normal condition when no liquid is in contact with the sensor head by detecting a certain amount of light exiting the sensor head, and
    determining a malfunction condition when liquid is in contact with the sensor head by detecting an amount of light, less than the certain amount of light, exiting the sensor head.

2. The method of claim 1, wherein the sensor head includes a body having first and second opposing ends, a plurality of perforations through the body and spaced between the first and second ends, and a mirror disposed at the second end, the perforations being constructed and arranged to receive and hold liquid therein, and wherein the normal condition is determined when only air is in the perforations, and the malfunction condition is determined when liquid is in at least some of the perforations.

3. The method of claim 1, wherein the liquid is water and/or oil.

4. The method of claim 1, wherein the step of providing the light source provides a light emitting diode disposed outside of the tank and optically connected to the sensor head via a fiber optic cable.

5. The method of claim 1, wherein the steps of detecting light include using a light detector disposed outside of the tank and optically connected to the sensor head via a fiber optic cable.

* * * * *